United States Patent
Brown et al.

(10) Patent No.: US 8,961,531 B2
(45) Date of Patent: Feb. 24, 2015

(54) INTRAOCULAR LENS TRANSFER CASE

(75) Inventors: Kyle Brown, Fort Worth, TX (US);
Dengzhu Yan, Northborough, MA (US);
David Downer, Fort Worth, TX (US)

(73) Assignee: Novartis AG, Basel (CH)

( * ) Notice: Subject to any disclaimer, the term of this patent is extended or adjusted under 35 U.S.C. 154(b) by 147 days.

(21) Appl. No.: 13/328,744

(22) Filed: Dec. 16, 2011

(65) Prior Publication Data

US 2012/0158007 A1   Jun. 21, 2012

Related U.S. Application Data

(60) Provisional application No. 61/424,883, filed on Dec. 20, 2010.

(51) Int. Cl.
*A61F 9/00*   (2006.01)
*A61F 2/16*   (2006.01)

(52) U.S. Cl.
CPC ............. *A61F 2/1691* (2013.01); *A61F 2/1678* (2013.01); *A61F 2/167* (2013.01)
USPC ......................................... 606/107; 623/6.12

(58) Field of Classification Search
USPC .................................. 606/107, 166; 623/6.12
See application file for complete search history.

(56) References Cited

U.S. PATENT DOCUMENTS

| | | | |
|---|---|---|---|
| 4,681,102 A * | 7/1987 | Bartell | 606/1 |
| 5,275,604 A | 1/1994 | Rheinish et al. | |
| 5,290,892 A | 3/1994 | Namdaran et al. | |
| 5,494,484 A | 2/1996 | Feingold | |
| 5,499,987 A | 3/1996 | Feingold | |
| 5,616,148 A * | 4/1997 | Eagles et al. | 606/107 |
| 5,620,450 A * | 4/1997 | Eagles et al. | 606/107 |
| 5,643,276 A | 7/1997 | Zaleski | |
| 5,653,715 A | 8/1997 | Reich et al. | |
| 5,810,834 A * | 9/1998 | Heyman | 606/107 |
| 5,873,879 A * | 2/1999 | Figueroa et al. | 606/107 |
| 5,947,976 A * | 9/1999 | Van Noy et al. | 606/107 |
| 6,010,510 A * | 1/2000 | Brown et al. | 606/107 |
| 6,083,231 A | 7/2000 | Van Noy et al. | |

(Continued)

FOREIGN PATENT DOCUMENTS

FR   2935606 A1   3/2010
WO   10028873 A1   3/2010

OTHER PUBLICATIONS

EP11850568.4, "Supplementary European Search Report", European Patent Office, Sep. 30, 2014, 7 pgs.

(Continued)

*Primary Examiner* — David Eastwood
(74) *Attorney, Agent, or Firm* — Jason Finch

(57) ABSTRACT

An intraocular lens (IOL) transfer case for transferring an IOL to an injection cartridge includes a lens holder for holding the IOL. The lens holder includes a bore. Folding members within the lens holder are configured to fold the IOL into a partially folded position when the IOL is slid through the bore across the folding members. The IOL transfer case also includes an interface configured to removably connect to an injection cartridge. The interface is positioned to deliver the IOL in the partially folded position within the injection cartridge when the interface is connected to the injection cartridge. The IOL transfer case also includes a plunger connected to the lens holder and configured to push the IOL in the partially folded position through the bore to deliver the IOL into the injection cartridge.

8 Claims, 4 Drawing Sheets

(56) References Cited

U.S. PATENT DOCUMENTS

| | | | |
|---|---|---|---|
| 6,143,001 A | 11/2000 | Brown et al. | |
| 6,468,282 B2* | 10/2002 | Kikuchi et al. | 606/107 |
| 6,537,283 B2* | 3/2003 | Van Noy | 606/107 |
| 6,554,839 B2* | 4/2003 | Brady | 606/107 |
| 7,014,641 B2* | 3/2006 | Kobayashi et al. | 606/107 |
| 7,156,854 B2 | 1/2007 | Brown et al. | |
| 7,905,888 B2* | 3/2011 | Brown | 606/107 |
| 2002/0151904 A1* | 10/2002 | Feingold et al. | 606/107 |
| 2004/0215207 A1* | 10/2004 | Cumming | 606/107 |
| 2004/0243141 A1* | 12/2004 | Brown et al. | 606/107 |
| 2006/0200167 A1* | 9/2006 | Peterson et al. | 606/107 |
| 2007/0060925 A1* | 3/2007 | Pynson | 606/107 |
| 2008/0147081 A1 | 6/2008 | Pynson | |
| 2008/0200920 A1* | 8/2008 | Downer | 606/107 |
| 2009/0318933 A1 | 12/2009 | Anderson | |
| 2010/0036385 A1 | 2/2010 | Isaacs et al. | |
| 2010/0161049 A1 | 6/2010 | Inoue | |
| 2012/0226286 A1* | 9/2012 | Weston et al. | 606/107 |

OTHER PUBLICATIONS

PCT/US2011/065574, "International Search Report", International Searching Authority, Oct. 4, 2012, 2pgs.

* cited by examiner

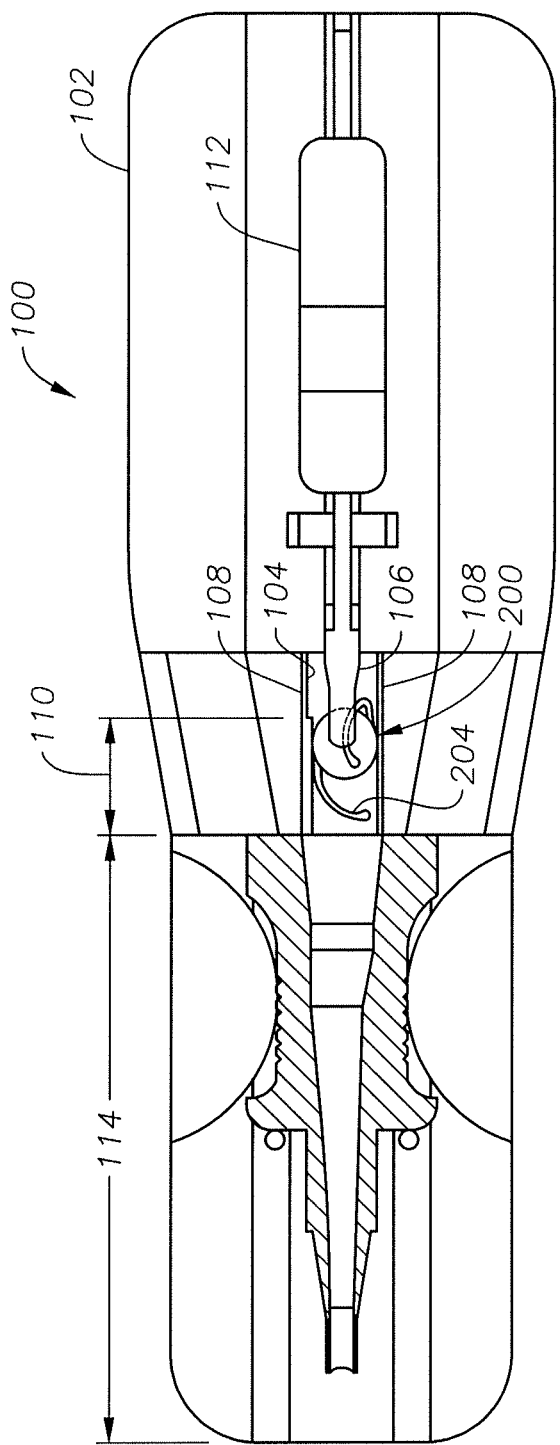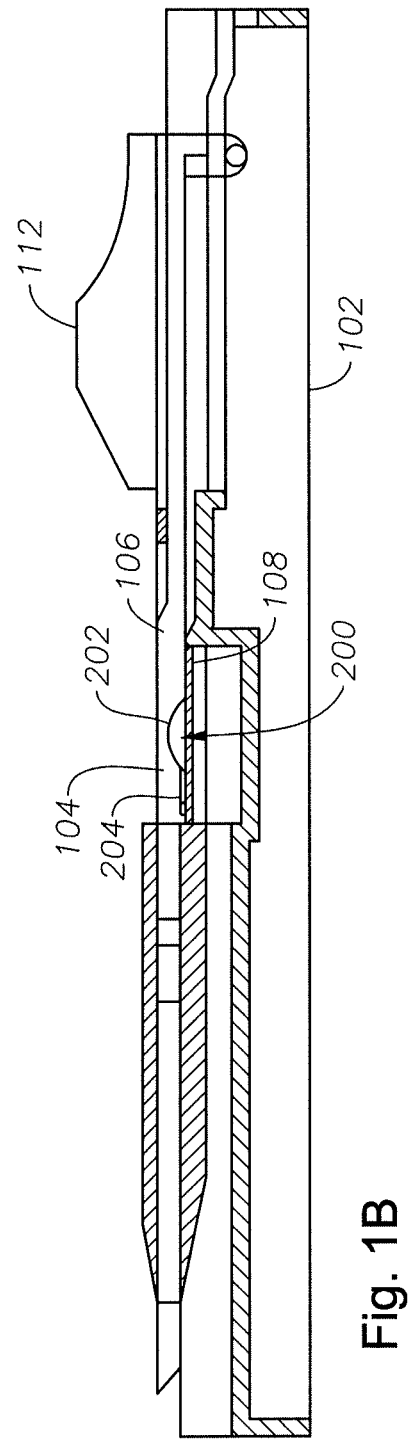

INTRAOCULAR LENS TRANSFER CASE

RELATED APPLICATIONS

This application claims priority to U.S. provisional application Ser. No. 61/424,883, filed on Dec. 20, 2010, the contents which are incorporated herein by reference.

FIELD OF THE INVENTION

This invention relates to intraocular lenses (IOLs) and more particularly to an IOL transfer case for loading an IOL into a cartridge.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens. When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger, such as the one described in U.S. Pat. No. 4,681,102 (Bartell), which includes a split, longitudinally hinged cartridge. Similar designs are illustrated in U.S. Pat. Nos. 5,494,484 and 5,499,987 (Feingold) and U.S. Pat. Nos. 5,616,148 and 5,620,450 (Eagles et al.). Other cartridge designs include, for example, U.S. Pat. No. 5,275,604 (Rheinish et al.) and U.S. Pat. No. 5,653,715 (Reich et al.).

In these prior art systems, an IOL is provided in a lens case from which the IOL is transferred into an injector cartridge, such as by using forceps. However, the step of transferring the lens from the case to the injector cartridge can inadvertently result in damage to the IOL, as in the cases where the optic of the IOL is scratched by the forceps or the haptics are torn off of the IOL. An alternative approach is to provide a preloaded injector, such as the one described in U.S. Pat. No. 7,156,854 (Brown et al.). In this case, there is not a separate loading step. However, such integrated injector systems are entirely disposable, and they are not compatible with reusable handpieces. Yet another alternative is to use a preloaded lens transfer case that uses a mechanism to transfer the IOL into a cartridge. But the existing lens transfer cases involve relatively complicated mechanical transfer mechanism in order to keep the lens in the correct loading position and to make sure that the IOL is correctly transferred to the cartridge.

BRIEF SUMMARY OF THE INVENTION

In particular embodiments of the present invention, an intraocular lens (IOL) transfer case for transferring an IOL to an injection cartridge includes a lens holder for holding the IOL. The lens holder includes a bore. Folding members within the lens holder are configured to fold the IOL into a partially folded position when the IOL is slid through the bore across the folding members. The IOL transfer case also includes an interface configured to removably connect to an injection cartridge. The interface is positioned to deliver the IOL in the partially folded position within the injection cartridge when the interface is connected to the injection cartridge. The IOL transfer case also includes a plunger connected to the lens holder and configured to push the IOL in the partially folded position through the bore to deliver the IOL into the injection cartridge.

In other embodiments of the present invention, a method of transferring an IOL from a lens transfer case to an injection cartridge includes providing a lens transfer case comprising a lens holder, a bore within the lens holder, and folding members within the bore configured to fold the IOL into a partially folded position when the IOL is slid across the folding members. The method further includes removably connecting an injection cartridge to the lens transfer case, releasing the IOL from a rest position in the lens transfer case, sliding the IOL across the folding members to fold the IOL into the partially folded position, pushing the IOL in the partially folded position through a distal end of the bore into the injection cartridge, and disconnecting the lens transfer case from the injection cartridge.

Other features of the present invention will become apparent with reference to the drawings, and the following description of the drawings and claims.

BRIEF DESCRIPTION OF THE DRAWINGS

FIGS. 1A and 1B illustrate an intraocular lens transfer case according to a particular embodiment of the present invention;

DETAILED DESCRIPTION OF THE INVENTION

Figure 2:
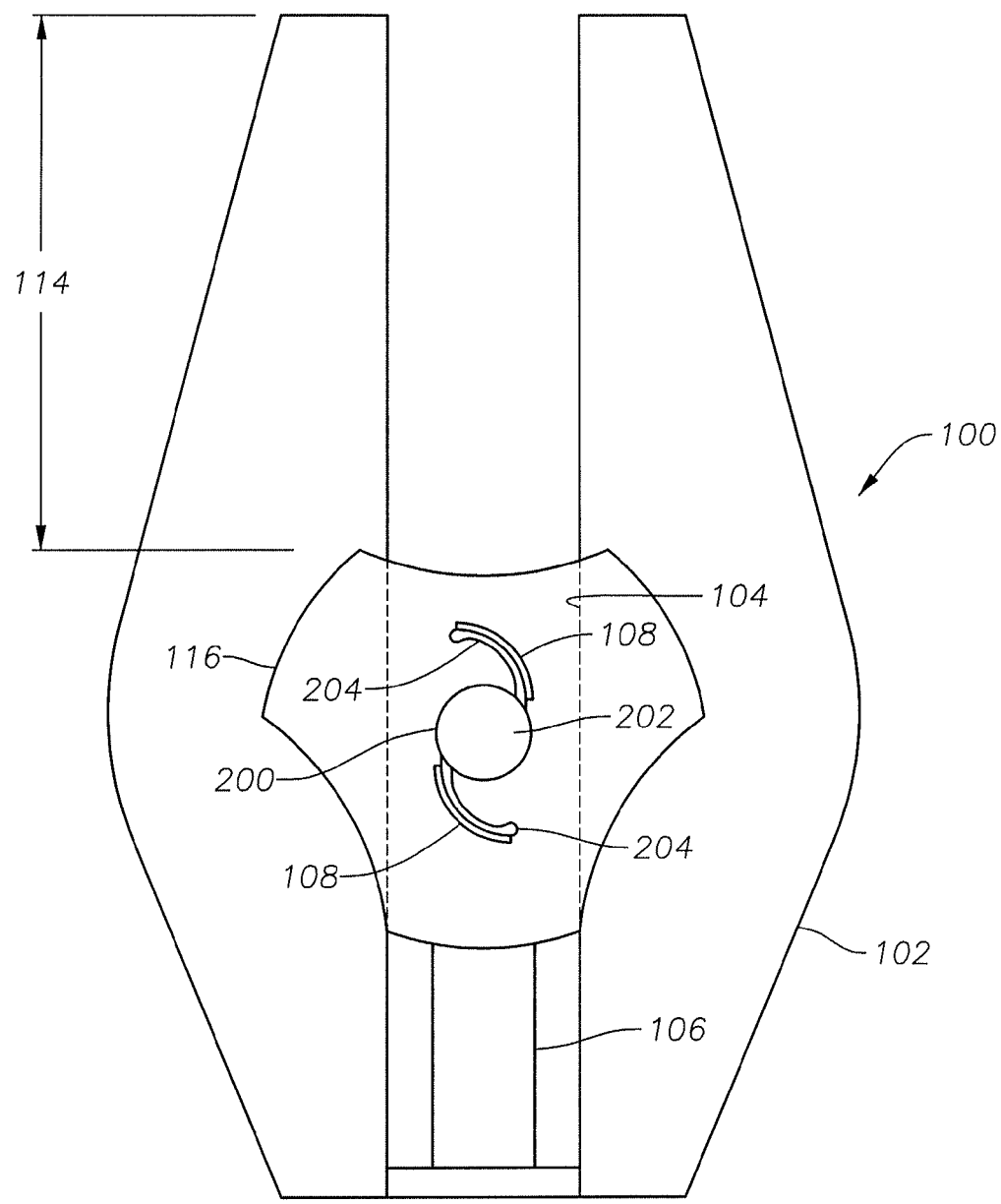
FIG. 2 shows an alternative lens transfer case according to another embodiment of the present invention.

FIGS. 1A and 1B show top and side cross-sectional views of an intraocular lens transfer case 100 according to a particular embodiment of the present invention. The delivery system 100 includes a lens holder 102 having a bore 104 along with a plunger 106 to advance an intraocular lens within the lens holder 102. The lens holder 102 may be any portion, components, or collection of components holding an intraocular lens (IOL) 200 for transportation that does not include a nozzle portion for injecting the IOL 200 through an incision. The term "plunger" describes any component advanced through the bore 104 to push an intraocular lens through the injector body, which can be (but need not be) connected to other components of the intraocular lens transfer case 100. In particular embodiments, the entire lens transfer case 100 may be formed as a single piece from a suitable material, which may include, for example, polypropylene or polyethylene. Various embodiments may also include a lubricious coating within the bore 104 of the injector body 102 to facilitate advancement of the intraocular lens. The lens transfer case 100 may also be filled with a viscoelastic material or a liquid (such as balanced saline solution) in order to facilitate movement of the IOL 200 through the lens transfer case 100.

Various embodiments of an inventive lens transfer case 100 provide an improved method and system for transferring an IOL 200 from the lens transfer case to a cartridge for injection. Such embodiments may advantageously allow the use of existing cartridges and reusable handpieces while simultaneously removing handling of the lens with forceps during lens transfer. This is turn reduces the likelihood of lens damage and provides a more controlled transfer process. But unlike previous lens transfer cases, various embodiments of an inventive lens transfer case 100 fold the IOL 200 by sliding the IOL 200 down within the bore not only during the IOL injection procedure but also during the transfer of the IOL 200 from the lens transfer case 100 to the cartridge. In certain embodiments, the familiarity of the plunger-and-bore system can then be leveraged in the lens transfer operation, but it can also incorporate advantages of preloaded lens transfer cases that had previously not been realized in combination with cartridge and handpiece systems that provide a complete and continuous folding operation through the bore. The counter-intuitive separation of the plunger-and-bore operations into two separate steps, a transfer step and a loading step, thus allows advantages of both a preloaded lens transfer case and a reusable handpiece to be achieved effectively.

The IOL 200 may be any intraocular lens formed of a flexible material, including but not limited to hydrogels, silicone, or acrylic materials, such as the cross-linked acrylic material described in U.S. Pat. No. 5,290,892 (known under the trademark AcrySof®). The IOL 200 includes at least one optic 202 structured to focus light onto a patient's retina in any manner, including the use of any suitable refractive and/or diffractive elements, along with one or more haptics 204 that stably fixate the IOL 200 within the anatomy of the eye when implanted. Various embodiments of an inventive lens transfer case 100 allow the IOL 200 to rest on folding members 108 on a floor of the bore 104 of the lens holder 102. "Bottom" in the context of the lens transfer case 100 refers to the side corresponding to the downward facing side of the cartridge during injection of the IOL 200, regardless of the particular orientation in which the lens transfer case 100 happens to be held, although the bottom would ordinarily be on the underside of the cartridge as held by a person operating the lens transfer case 100.

The folding members 108 are structures configured such that when the IOL 200 is slid across the folding members 108, the IOL 200 is reconfigured into at least a partially folded position. Examples of structures that can be used as folding members 108 include the various folding mechanisms described in U.S. Pat. Nos. 5,947,976; 6,083,231; and 6,143,001, all of which are incorporated herein by reference. For example, one of the folding members 108 can be an asymmetric ramp in the floor of the bore 104 to direct folding in a particular direction. The folding members 108 may also include raised cams, rails, pegs, and/or shelves to force the haptics 204 into a particular orientation as they are slid across the folding members 108. Similarly, the cams or rails can hold the optic 202 in a folded position while the haptics 204 are directed to the folded configuration.

In the embodiment of FIG. 1, the lens transfer case 100 includes a bore 104 having a narrowed region 110 at a distal end of the bore 104. In the context of the lens transfer case 100, "proximal" refers to the direction away from the advancement of the IOL 200 into the cartridge, while "distal" refers to the direction in which the IOL 200 advances to the cartridge, which would ordinarily correspond to the directions closer and farther away from the person operating the lens transfer case 100. The narrowing diameter of the bore 104 causes the IOL 200 to fold upon itself as the IOL 200 is advanced through the bore. The folding structures 108 direct the folding of the optic 202 and the haptics 204 into the desired folded configuration.

The plunger 106 is used to advance the IOL 200 through the bore 104. The plunger 106 may include a soft tip to reduce the likelihood of damage to the IOL 200 as the IOL 200 is urged forward through the bore 104. In the depicted embodiment, the plunger 106 includes a thumb slide 112 that is pushed distally by the operator to move the plunger 106 forward. Alternative embodiments could use any other suitable technique for advancing the plunger, including, for example, a syringe-style plunger that may include a thumb ring, a knob that is turned to advance a plunger in threaded engagement with the bore 104, or even a motorized injector that is triggered electronically. In general, any manner of slidably advancing the IOL 200 through the bore 104 across the folding members 108 could in principle be compatible with particular embodiments of the lens transfer case 100. The plunger 106 may also be biased in one direction or the other, such as by placing a ramp in the bore 104, and the plunger 106 may also have an tip offset from a central axis of the plunger 106, with such modifications tending to push the IOL 200 preferentially in one direction.

At the distal end of the lens transfer case 100 is an interface 114. The interface 114 is configured to connect to the injection cartridge so that the partially folded IOL 200 is appropriately situated within the injection cartridge following the transfer. Thus, for example, a delivery end of the lens transfer case 100 could be partially inserted into a nozzle of the injection cartridge so that when the partially folded IOL 200 is transferred into the injection cartridge, the nozzle maintains the IOL 200 in its partially folded position. The interface 114 may also include recesses generally conforming to the shape of at least part of the injection cartridge, locking features (such as releasable hooks or tab-and-slot features), or other suitable receiving structures to receive and position the injection cartridge relative to the lens transfer case 100. Before or after connection to the lens transfer case 100, the injection cartridge may also be treated with a viscoelastic material, liquid, and/or a lubricious coating in order to facilitate advancement of the IOL 200 within the injection cartridge.

Before the lens transfer case 100 is used for transferring the IOL 200, it is desirable for the IOL 200 to be held in a rest position and preferably in an unfolded position. U.S. Pat. No. 7,156,854 describes an intraocular lens delivery system having a stop frictionally engaged on a lid of the IOL delivery system to prevent movement of an IOL within the delivery system. A similar structure could likewise be placed on the top of the lens transfer case 100 in order to maintain the IOL 200 in the rest position before the IOL 200 is transferred to the injection cartridge. Alternatively, a stop extending upwardly from the floor of the lens holder 102 could hold the IOL 200 in place, and the stop could be disengaged by the use of a control, such as a button or a switch. In general, any other structures or techniques for maintaining the IOL 200 in a suitable rest condition could also be suitably adapted for use with the lens transfer case 100.

One such embodiment of the lens transfer case 100 is depicted in FIG. 2. In the depicted embodiment, the lens transfer case 100 includes a cap 116 that holds the IOL 200 in position. In order to perform the lens transfer operation, the cap 116 is pressed downward in order to urge the IOL 200 onto folding structures 108 on the bottom of the lens transfer case 100. The cap 116 is then twisted to rotate the lens, as shown by the arrow in FIG. 2, sliding it across the folding members 108 in order to fold the lens. The cap 114 is then removed to release the folded IOL 200, and the plunger 106 slidably advances the folded IOL 200 past the folding members 108 through the bore 104 and into the injection cartridge. Using a cap 114 is only one alternative method to fold the lens along with the plunger 106, and other alternative embodiments could involve different techniques to release the IOL 200 and to begin the folding process, such as by using side buttons that push against the sides of the IOL 200 to cause an initial fold. In general, any structure capable of sliding the IOL 200 against folding structures 108 in a desired configuration could be implemented in various embodiments of the present invention.

Figure 3:
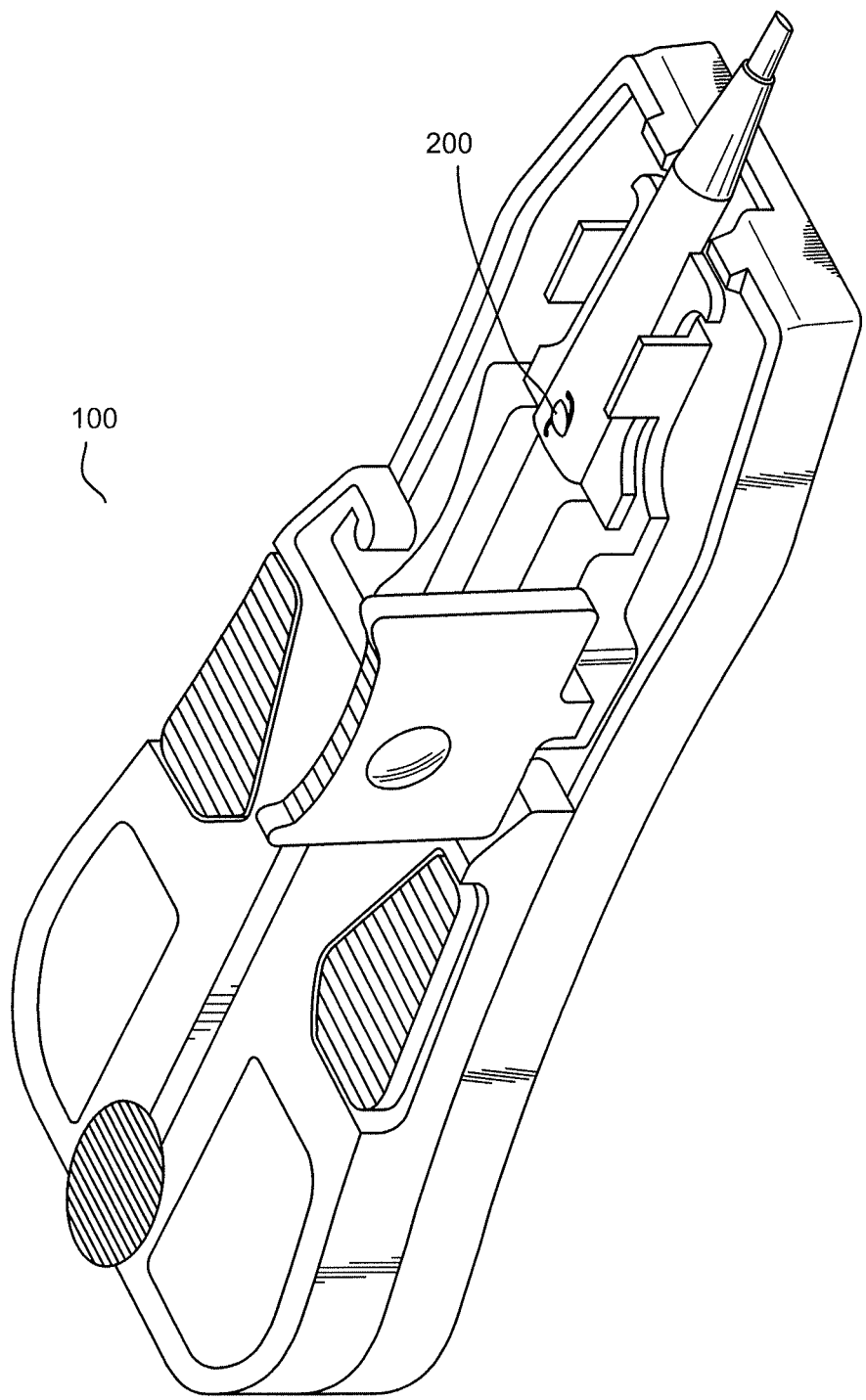
FIG. 3 is a top level assembly view of a lens transfer case according to a particular embodiment of the present invention.

FIG. 3 is a top level assembly view of a particular embodiment of lens transfer case 100. In the depicted embodiment, the lens transfer case 100 includes a hinged lid that closes to form the bore 104 surrounding the IOL 200. The hinged lid may include additional features to facilitate folding of the IOL 200 in cooperation with folding features 108, such as features to guide the haptics. The hinged lid is useful to allow the IOL 200 to be inserted into the lens transfer case 100 during the assembly process. Although the lid is shown as hinged, any suitable attachment method for a cap, such as friction fitting or the like, may also be employed. The depicted embodiment also shows thumb triggers that are depressed to release the IOL 200 from a rest position.

Figure 4:
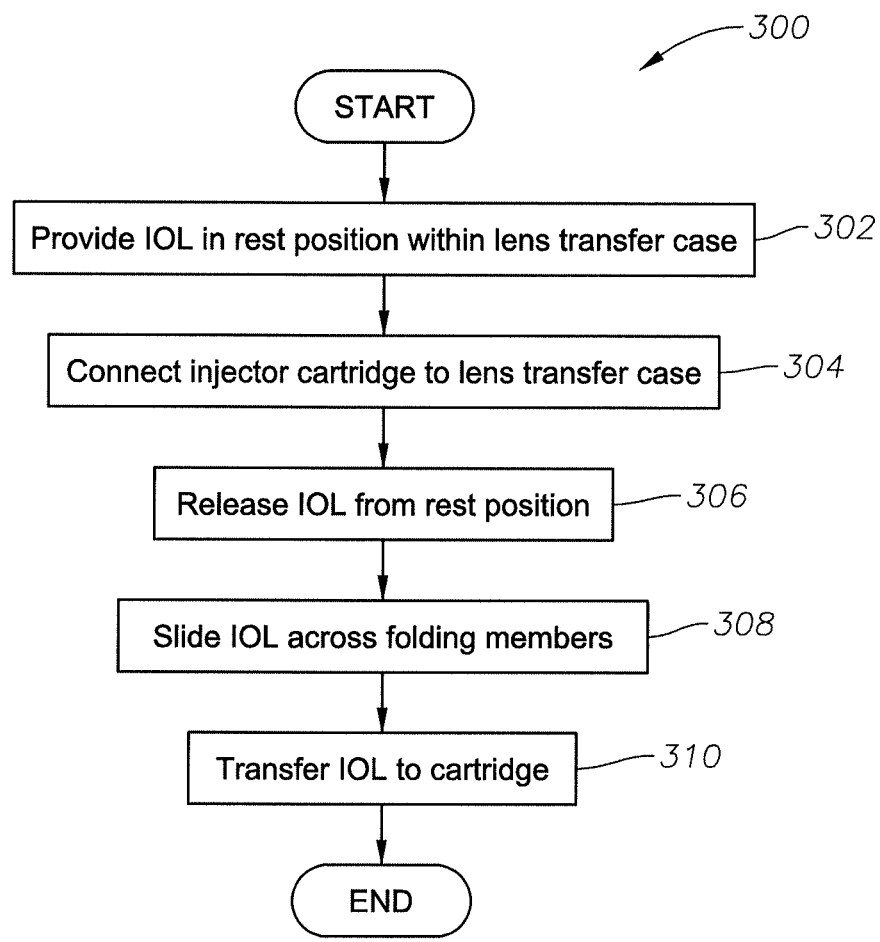
FIG. 4 is a flowchart showing an example method of transferring an IOL from a lens transfer case to an injection cartridge.

FIG. 4 is a flow chart 300 illustrating an example lens transfer method according to a particular embodiment of the present invention. At step 302, an IOL 200 is provided in a rest position within a lens transfer case 100 having folding members 108 at the bottom of the lens transfer case 100. At step 304, an injector cartridge is connected to the lens transfer case 100. Depending on the particular operation of the lens transfer case 100, the injector cartridge could also be connected to the lens transfer case 100 after other steps are performed.

At step 306, the IOL 200 is released from the rest position. Then, at step 308, the IOL 200 is slid across the folding members 108 in order to partially fold the IOL 200. In one example, the IOL 200 may be released by removing a stop frictionally engaged on a top of the lens transfer case 100 at step 306, and the IOL 200 may then be slid across the folding members 108 at step 308 by urging the IOL 200 distally with a plunger 106. In another example, the IOL 200 may be released from the rest position by pressing the IOL 200 downward onto the folding members 108 using a cap 114 at step 306, and the IOL 200 may be slid across the folding members 108 at step 308 by twisting the cap 114 to rotate the IOL 200, after which the cap 114 may be withdrawn from the IOL 200.

At step 310, the IOL 200 is transferred from the lens transfer case 100 to the injection cartridge. In one example, the IOL 200 may be transferred continuously as part of the folding step 308. In another example, the IOL 200 may be transferred in a separate step after the IOL 200 has already been previously folded. In general, any method that involves partially folding the IOL 200 by sliding the IOL 200 across folding members 108 before transfer to the injection cartridge may suitably be adapted for use with various embodiments of the present invention.

While certain embodiments of the present invention have been described above, these descriptions are given for purposes of illustration and explanation. Variations, changes, modifications and departures from the devices and methods disclosed above may be adopted without departure from the scope of the present invention as claimed.

What is claimed is:

1. An intraocular lens (IOL) transfer case for transferring an IOL to an injection cartridge, comprising:
    a lens holder for holding the IOL including a bore;
    an inner surface of the bore comprising folding members configured to fold the IOL into a partially folded position when the IOL is slid through the bore across the folding members;
    an interface configured to removably connect to an injection cartridge while the injection cartridge is separate from a handpiece that facilitates injection of the IOL from the injection cartridge into a patient's eye, wherein the interface is positioned to deliver the IOL in the partially folded position into the injection cartridge when the interface is connected to the injection cartridge and the injection cartridge is configured to disconnect from the interface while leaving the IOL in the partially folded position to allow the injection cartridge to be connected to a handpiece such that the IOL can be injected from the injection cartridge into a patient's eye; and
    a plunger connected to the lens holder and configured to push the IOL through the bore, across the folding members, and into the partially folded position to deliver the IOL into the injection cartridge, wherein a longitudinal axis of the plunger is substantially aligned with a longitudinal axis of the injection cartridge.

2. The IOL transfer case of claim 1, wherein the folding members comprise at least one ramp asymmetrically positioned within the bore.

3. The IOL transfer case of claim 1, further comprising a cap, the cap configured to hold the IOL in a rest position.

4. The IOL transfer case of claim 3, wherein the cap is frictionally engaged on a top of the lens holder.

5. The IOL transfer case of claim 3, wherein the cap urges the IOL against the folding members when depressed and slides the IOL across the folding members when turned.

6. The IOL transfer case of claim 1, wherein the plunger comprises a thumb slide used to advance the plunger through the bore.

7. The IOL transfer case of claim 1, wherein the interface comprises a recess generally conforming to a shape of the injection cartridge.

8. The IOL transfer case of claim 1, wherein the interface comprises locking features configured to lock the injection cartridge in position when the interface is connected to the injection cartridge.

* * * * *